Oct. 4, 1960 E. R. GAGE Plant Pat. 1,975
APPLE TREE
Filed May 11, 1959
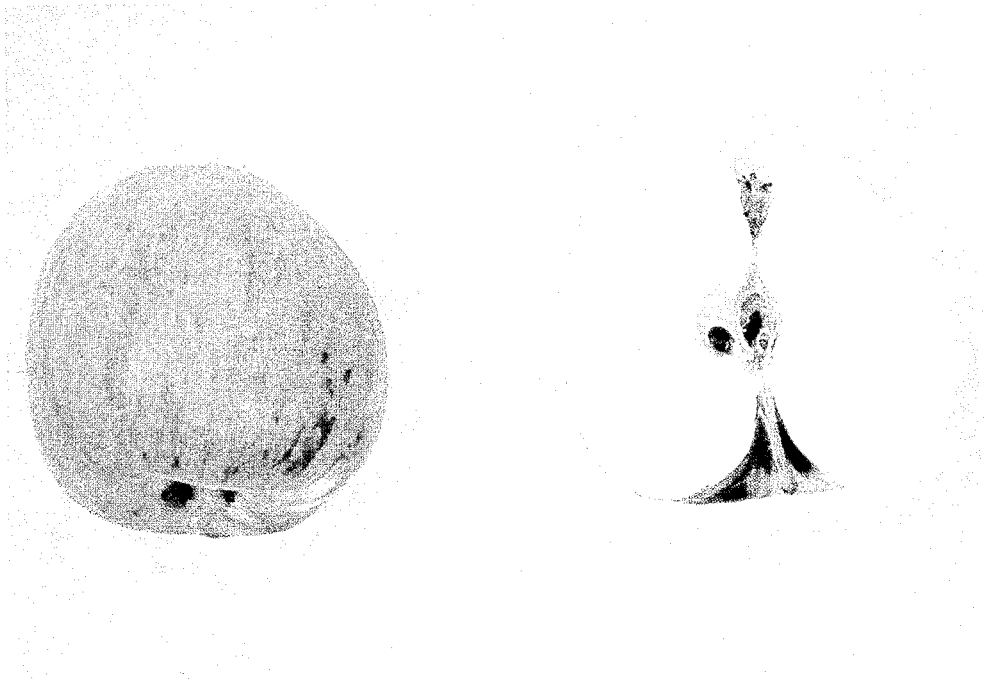

United States Patent Office

Plant Pat. 1,975
Patented Oct. 4, 1960

1,975

APPLE TREE

Ennals Ralph Gage, Mount Vernon, Wash., assignor to Sherm Fox, Bow, Skagit County, Wash.

Filed May 11, 1959, Ser. No. 812,570

1 Claim. (Cl. 47—62)

The present invention relates to a new and distinct variety of apple tree which was discovered by me as a newly found seedling on my cultivated property at 109 Front Street, Mount Vernon, Skagit County, Washington.

At the time of my discovery, my attention was attracted to the new variety by the fact that it was growing in my cultivated garden and out of curiosity, I took steps to preserve the small originally discovered plant, keep it under observation, and later have it asexually reproduced on my behalf. These observations and asexual reproductions as performed by grafting and budding at the Fir Island Nursery near Mount Vernon, Washington, conclusively established that the new variety was characterized by an outstanding flavor and keeping qualities.

More specifically, my new apple tree is particularly characterized as to novelty by the unique combination of good color, size, quality and flavor of the fruit, with a general resemblance of the fruit to that of the variety Gravenstein (unpatented) but having a more global form like the King (unpatented) and a distinct tarty flavor of its own. My new apple tree blooms approximately the same time as the Gravenstein (unpatented) but the maturing date is approximately four to six weeks later than the variety Gravenstein (unpatented).

While the actual parentage of the new variety is not known, it is definitely differentiated from all other varieties of which I am aware and is endowed with a unique and desirable combination of characteristics which is particularly valuable from a commercial standpoint and has heretofore never been available to the best of my knowledge.

Although generally resembling the varieties Gravenstein (unpatented) and King (unpatented), my new variety is definitely differentiated therefrom as well as from all other varieties of which I am aware. One of the principal differences which is highly valuable from a commercial standpoint is the fact that the fruit of my new variety matures from four to six weeks later than that of the Gravenstein (unpatented) although the season for bloom of each variety is substantially the same.

The flavor and color of my new variety generally resembles those of the Gravenstein (unpatented) but the fruit of my new apple tree is broader. The color of the skin of my new variety is striped red with a yellow background. In flavor the fruit of my new variety is slightly more acid and hence superior for culinary purposes. The fruit of my new variety is generally larger than that of the Gravenstein (unpatented) and the King (unpatented).

With regard to the characteristics of the tree of my new variety, the crotch angles and distributions of fruiting wood are superior and better than those of the Gravenstein (unpatented) and the King (unpatented).

Asexual reproductions of my new variety by budding and grafting show that the foregoing characteristics and distinctions come true to form and are established and transmitted through succeeding propagations.

The following is a detailed description of my new variety with color terminology in accordance with Ridgway's Color Standards and Nomenclature, and with the Horticultural Color Guide:

Dates of first and last picking: October 10th and October 24th.

Tree: Medium size; very vigorous; spreading; open; round topped; rapid grower, hardy, productive; regular bearing.

*Trunk.*—Medium stockiness; medium smoothness.

*Branches.*—Medium thick; smooth; much branched.

*Leaves.*—Size—large; color—Spinach Green, Plate 10960, page 200, vol. 2, Horticultural Color Guide.

Flowers: Dates of first and full blooms, April 10th and April 15th. Medium early classification. Size—medium; color—white.

Fruit: Maturity when described. Medium hard ripe; latter part of October.

*Size.*—Uniform; axial diameter about 3¾ inches; transverse diameter about 4¼ inches.

*Skin.*—Thick, tough, smooth waxed with many small even circular conspicuous dots colored pale Ochraeceous Buff (Plate XV, Color No. 15′, tone F (Ridgway's) fairly uniformly distributed). Color marking—stripes of Carmine, Plate 21, page 21, vol. 1, Horticultural Guide.

*Shape.*—Conical; truncate at base and apex; ribbed.

*Stem.*—Clubbed and medium stout; pubescent. Length from ½ inch to ⅞ inch. Breadth—7/32 inch. Markings — Vanaceous Russet, Plate XXVIII, Color No. 7′ (Ridgway).

*Eye.*—Large, open.

*Skin.*—Thick, tough; smooth; waxed with many small, even circular conspicuous dots colored Pale Ochraeceous Buff, Plate XV, Color No. 15′, tone F (Ridgway) fairly uniformly distributed. Ground color—Citron Yellow, Plate XVI, Color No. 23′, tone B (Ridgway); color markings—striped with Carmine, Plate 21, page 21, vol. 1 (Horticultural Guide).

*Flesh.* — Juicy; color—pale Chalcedony Yellow, Plate XVII, Color No. 25′, tone F (Ridgway). Texture—firm, fine, from crisp to melting. Flavor—tarty; rich. Aroma—distinct. Quality—Excellent.

*Seeds.*—Number—4 perfect; 1 per cell. Length—10/32 inch. Breath—4/16 inch. Form—obtuse. Color—Mars Brown, Plate XV, Color No. 13′, tone M (Ridgway).

Use: Market; dessert; culinary.

Keeping qualities: Excellent.

I claim:

A new and distinct variety of apple tree substantially as herein described, characterized particularly as to novelty by its superior crotch angles and distributions of fruiting wood and improved annual bearing habit, late maturing habit of its fruit, general similarity of its flavor, color and shape of its fruit to those of the variety Gravenstein (unpatented) but the fruit being distinguished from the Gravenstein (unpatented) by its tarty, acid flavor, the fruit is larger than that of the variety King (unpatented) but with oiliness of skin similar to the aforementioned variety with excellent keeping qualities.

References Cited in the file of this patent

UNITED STATES PATENTS

P.P. 1,721 Mooney ---------- June 24, 1958
P.P. 1,777 Daniels ---------- Dec. 9, 1958